(12) United States Patent  (10) Patent No.: US 6,332,368 B1
Cash et al.  (45) Date of Patent: Dec. 25, 2001

(54) LIVE LINE INSULATION SAMPLING

(75) Inventors: Gregory Anthony Cash; Graeme Allan George; Andrej Krivda; Frank George Deabill; Paul Blackmore; David Birtwhistle, all of Brisbane (AU)

(73) Assignee: Queensland University of Technology (AU)

( * ) Notice: Subject to any disclaimer, the term of this patent is extended or adjusted under 35 U.S.C. 154(b) by 0 days.

(21) Appl. No.: 09/508,569

(22) PCT Filed: Jul. 14, 1999

(86) PCT No.: PCT/AU99/00570

§ 371 Date: Mar. 14, 2000

§ 102(e) Date: Mar. 14, 2000

(87) PCT Pub. No.: WO00/04365

PCT Pub. Date: Jan. 27, 2000

(30) Foreign Application Priority Data

Jul. 14, 1998 (AU) ................................................ PP4643

(51) Int. Cl.[7] .................................................. G01N 1/04
(52) U.S. Cl. .......................................... 73/864.41; 83/919
(58) Field of Search ........................ 83/919; 73/864.41, 73/104

(56) References Cited

U.S. PATENT DOCUMENTS 3,599,297 * 8/1971 Seivers ........................... 24/132 WS
3,606,470 * 9/1971 Blum ..................................... 299/67
3,617,473 * 11/1971 Lipscomb, II .......................... 208/14
4,236,402 * 12/1980 McGuire ................................. 73/12
4,269,507 * 5/1981 Allen et al. ............................ 356/36
4,845,896 * 7/1989 Mercaldi .............................. 51/33 R
4,866,995 * 9/1989 Kaiser et al. ..................... 73/864.41
4,965,930 * 10/1990 Wnukowski ........................... 29/758
5,299,464 * 4/1994 Bennett ............................. 73/864.74
5,823,592 * 10/1998 Kalidindi ............................... 294/24

FOREIGN PATENT DOCUMENTS 31 36 770 A1   3/1983  (DE) .
2 280 133   *   1/1995  (GB) .............................. G01N/1/04

* cited by examiner

*Primary Examiner*—Hezron Williams
*Assistant Examiner*—C D Garber
(74) *Attorney, Agent, or Firm*—Burns, Doane, Swecker & Mathis, LLP

(57) ABSTRACT

A sampling tool is used to collect a sample from the surface of an insulator in a high voltage installation during live line conditions. The sampling tool comprises a sampling head mounted to one end of a hot stick. Sampling cartridges are interchangeably mountable to a pivoted block on the sampling head. The block is biased by a spring to urge the cartridge into contact with the surface of the insulator when a trigger on the sampling head comes into contact with the insulator. One cartridge includes a planing blade for collecting a sliver of material from the insulator surface. An alternative cartridge has a swab and an abrasive pad interchangeably insertable thereon for collecting a material sample from the insulator surface.

13 Claims, 5 Drawing Sheets

LIVE LINE INSULATION SAMPLING

THIS INVENTION relates to apparatus and method for live line sampling of insulation. In particular, the invention is directed to a tool for obtaining different types of samples from polymeric insulators in high voltage installations under live line conditions.

BACKGROUND ART

The insulators used in high voltage installations are prone to deterioration, particularly when exposed to harsh environmental conditions, such as strong sunlight and heat, for prolonged periods. Further, dust and other material accumulated on the insulation surfaces may provide a current path, leading to insulation breakdown. Proper preventative maintenance requires that the insulation be inspected regularly. New techniques of insulation condition monitoring require sampling of the insulator surface for laboratory analysis.

For obvious safety reasons, the high voltage power lines must be de-energised while such sampling or other contact occurs. Such power outages are not only inconvenient for electricity consumers, but also disruptive to the normal operation of power transmission systems.

It is an object of the present invention to provide apparatus and method for obtaining small samples of insulating material from high voltage installations under live line conditions.

SUMMARY OF THE INVENTION

In one broad form, the invention provides an apparatus for obtaining a sample from an insulator in a high voltage installation during live line conditions, the apparatus including a sampling head adapted to be mounted to one end of a hot stick in use, and a sampling device mounted to the sampling head, the sampling device being adapted to collect a sample from the surface of the insulator upon manipulation of the hot stick by a user remote from the sampling device.

The sampling device is typically a sampling cartridge. Preferably, different sampling cartridges are interchangeably mountable on the sampling head.

In the preferred embodiment, one particular type of sampling cartridge is adapted to obtain a sliver of material from an insulator. Another type of cartridge is designed to obtain surface material from the insulator.

The sampling head preferably has biasing means to urge the sampling device into contact with the surface of the insulator. In one embodiment, the sampling head has a pivoting block or turret on which the sampling device is mounted. The turret can be cocked against the bias of a spring, and released when the sampling head makes contact with part of the insulator. Upon release of the biased turret, it pivots and places the sampling device onto the surface of the insulator, the bias applied to the turret also serving to keep the sampling device on the surface of the insulator.

By moving the sampling head remotely via the hot stick, a sliver or surface sample (depending on the particular sampling device being used) can be obtained. The sample is normally retained in the sampling device for further analysis.

This application also discloses a method of obtaining samples from an insulator, using the abovedescribed apparatus.

In order that the invention may be more fully understood and put into practice, a preferred embodiment thereof will now be described with reference to the accompanying drawings.

DESCRIPTION OF PREFERRED EMBODIMENT

Figure 1:
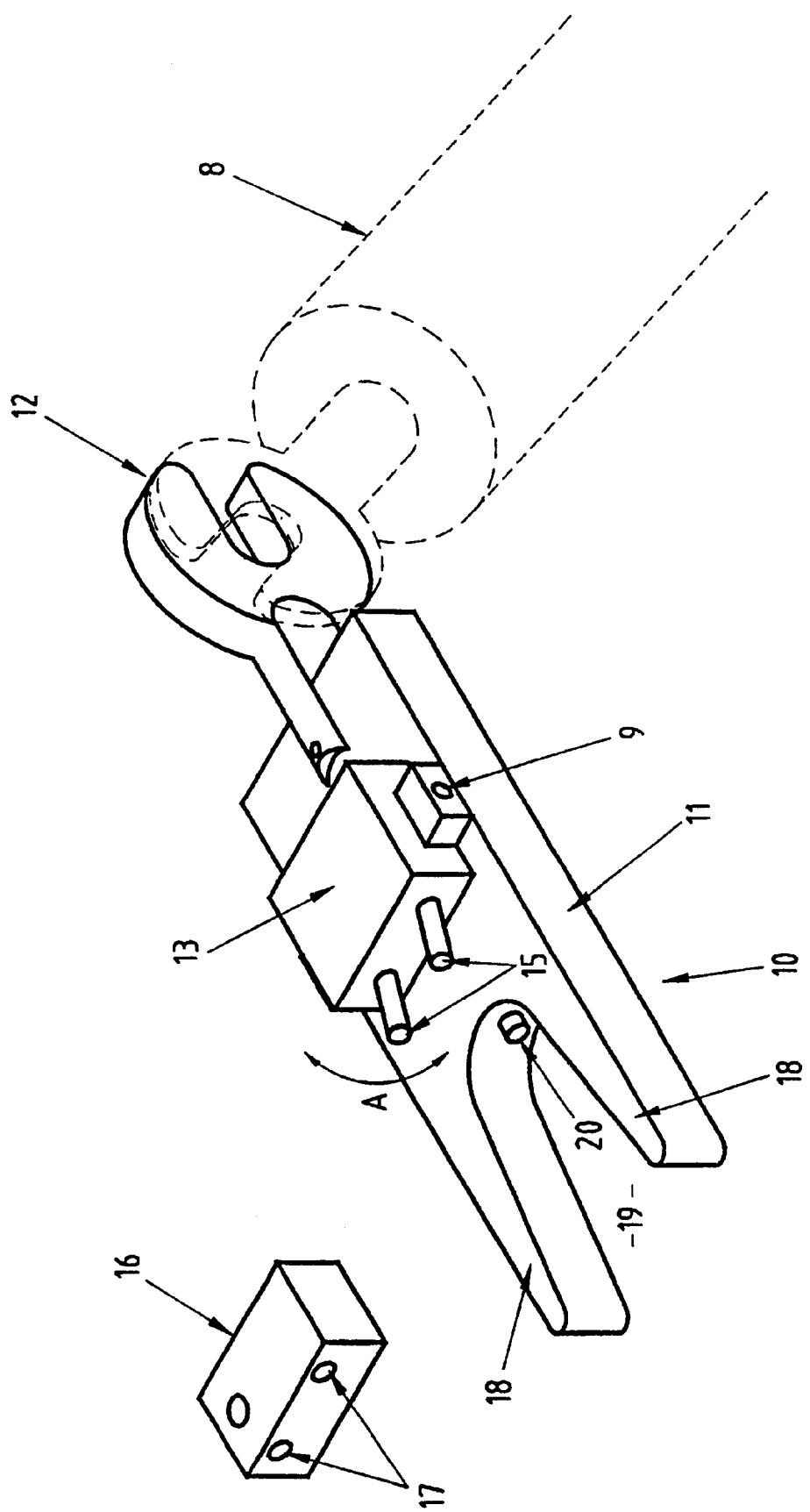
FIG. 1 is a perspective view of a sampling head of the tool of the preferred embodiment.

As shown in the drawings, a live line sampling tool comprises a sampling head 10 which is adapted to be mounted to a conventional "hot stick" 8 shown in broken outline. The hot stick 8 is a long insulated or nonconductive rod used for working on energised high voltage lines. Such hot sticks are well known in the art and need not be described in detail in this application. The sampling head 10 has a platform 11 with a hot stick fitting 12 at the rear end thereof, to enable the sampling head to be adjustably mounted to the hot stick.

Figure 2:
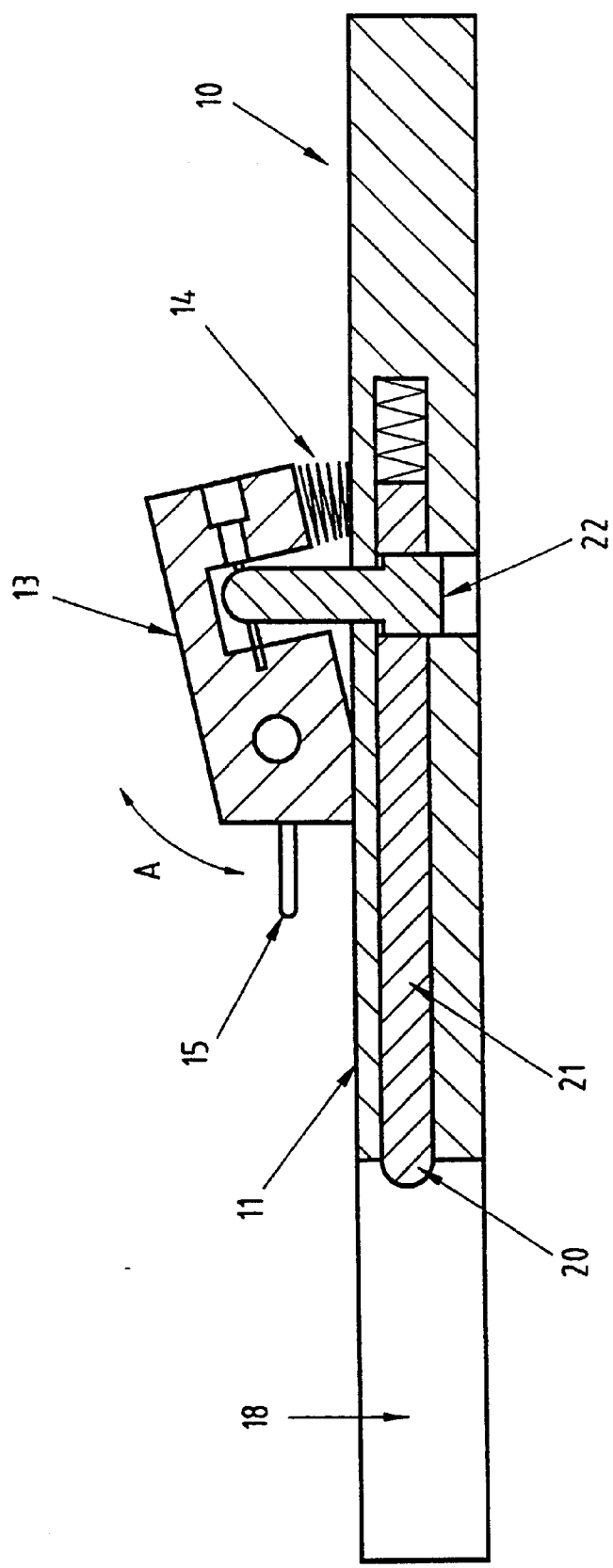
FIG. 2 is a longitudinal sectional view of the sampling head of FIG. 1, FIG. 3A and FIG. 3B are perspective views of alternative sampling cartridges suitable for use with the sampling head of FIG. 1.

A block or turret 13 is pivotally mounted to the platform 11. The turret 13 is biased about its pivot pin 9 in an anticlockwise direction (as viewed in FIG. 2) by a coil spring 14. Any other suitable biasing means, such as a leaf spring or elastomeric material, may be used.

The turret 13 has a pair of loading fingers or prongs 15 extending therefrom. A sampling cartridge 16 may be interchangeably mounted on the turret by locating the prongs 15 in corresponding bores 17 in the sampling cartridge. The sampling cartridges will be described in more detail later.

The platform 11, turret 13 and cartridge 16 are made of a suitable material, for example, metal.

The front end of the platform 11 is bifurcated to form a pair of fingers 18 spaced on either side of a recess 19. The bifurcated front end of the sampling head assists in locating the sampling head at an insulator. A release button 20 is located at the base of the recess 19, and is connected to a release rod 21 extending into the platform 11 as shown more clearly in FIG. 2. The release button is formed by the outer tip of the release rod, which is biased forwardly relative to the platform, i.e. the button 20 is biased into the recess 19 between the fingers 18.

The release rod 21 cooperates with a locking pin 22 which extends upwardly through the platform 11 into a recess in the turret 13. The locking pin is pivotally connected to the turret.

Various sampling cartridges may be used interchangeably with the sampling head 10. A first cartridge type 16A is shown in FIG. 3A. The cartridge 16A is constructed as a miniature wood plane, and has an inclined blade 23. In use, the cartridge 16A cuts a small sliver from the surface of an insulator shed. Typically, the sliver is about 10 mm×10 mm×0.3 mm.

To prevent damage to the sliver before and during cutting, the front bottom part of the cartridge preferably is approximately 1.5–2.0 mm above the bottom surface of the cartridge sides, i.e. about 1.5–2.0 mm above the polymer insulator surface in use. This is a particular advantage of this cartridge design. Pressure platen along the front part of the cartridge 16A ensure that a sufficient pressure is applied to enable the sample to be taken.

As the sliver is cut from the insulator, it curls up into the cartridge 16A. A cover 24 on the top of the plane-like cartridge 16A prevents the sliver from falling out of the cartridge.

Figure 3B:
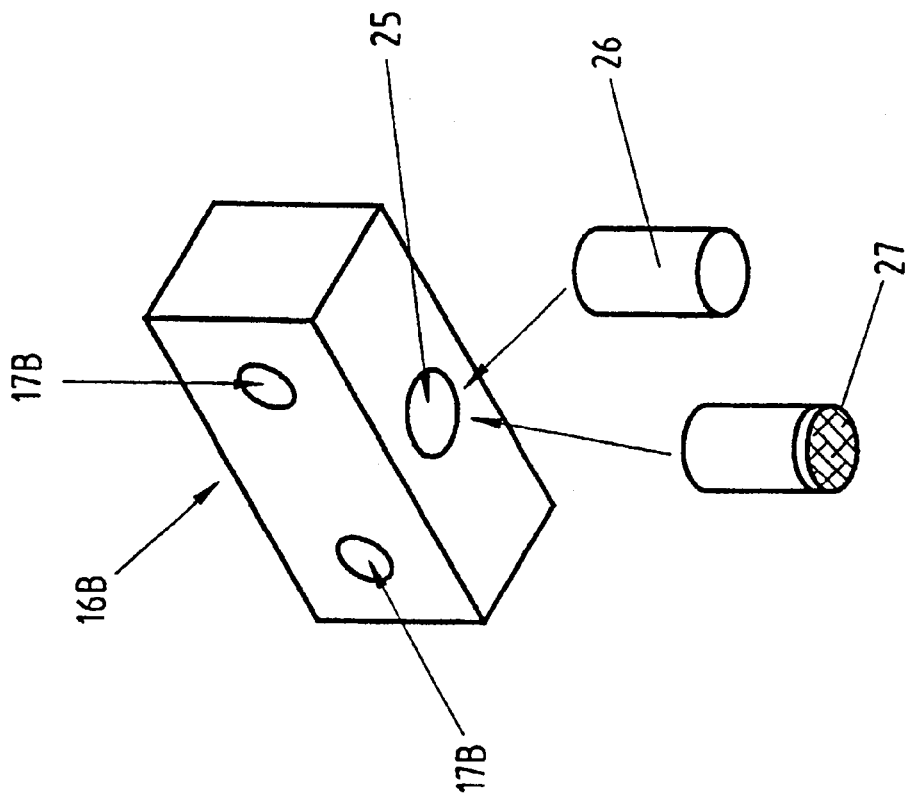
Figure 3A:
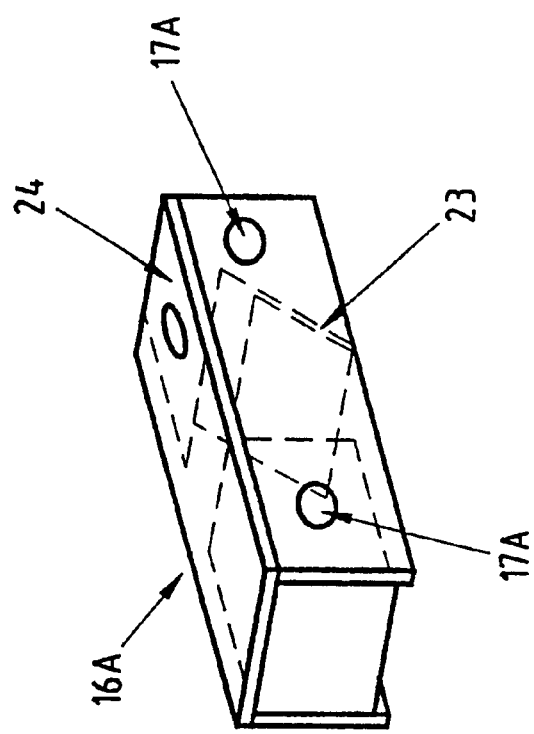

A second type of cartridge 16B is shown in FIG. 3B. The cartridge 16B has a socket 25 into which sampling inserts may be interchangeably inserted. For example, a cotton swab 26 dipped in a polymer solvent may be inserted in the socket 25, the bottom tip of the swab protruding from the underside of the cartridge 16B. As the cartridge moves on the surface of an insulator, polymer material present on the surface of the insulator is collected onto the cotton swab 26.

Further, or alternatively, an insert, such as a cylinder 27 with an abrasive pad on its underside can be inserted in the socket 25, such that the abrasive surface and a part of the insert protrudes from the underside of the cartridge 16B. As the cartridge moves on the surface of the insulator, the abrasive surface collects material present on the surface of the insulator.

In use, the sampling head 11 is mounted to a hot stick. The turret is "cocked" by normally pressing down on its rear end to cause it to pivot clockwise (FIG. 2) against the bias of spring 14. This causes the turret 13 to depress the locking pin 22 whereupon it is retained in its depressed position by the rod 21. The turret 13 is thereby held against the bias of spring 14. The appropriate sampling cartridge 16 is then loaded onto the sampling head 11 by locating it on the prongs 15 on the turret 13.

The sampling head on the end of the hot stick is then presented to an insulator 28 in live line conditions. The insulator 28 typically consists of a rod 29 and a number of sheds 30 extending radially from the rod 29. The prongs 18 of the platform 11 are located about the insulator rod under a shed 30, so that the shed rests on the platform 11.

Figure 4:
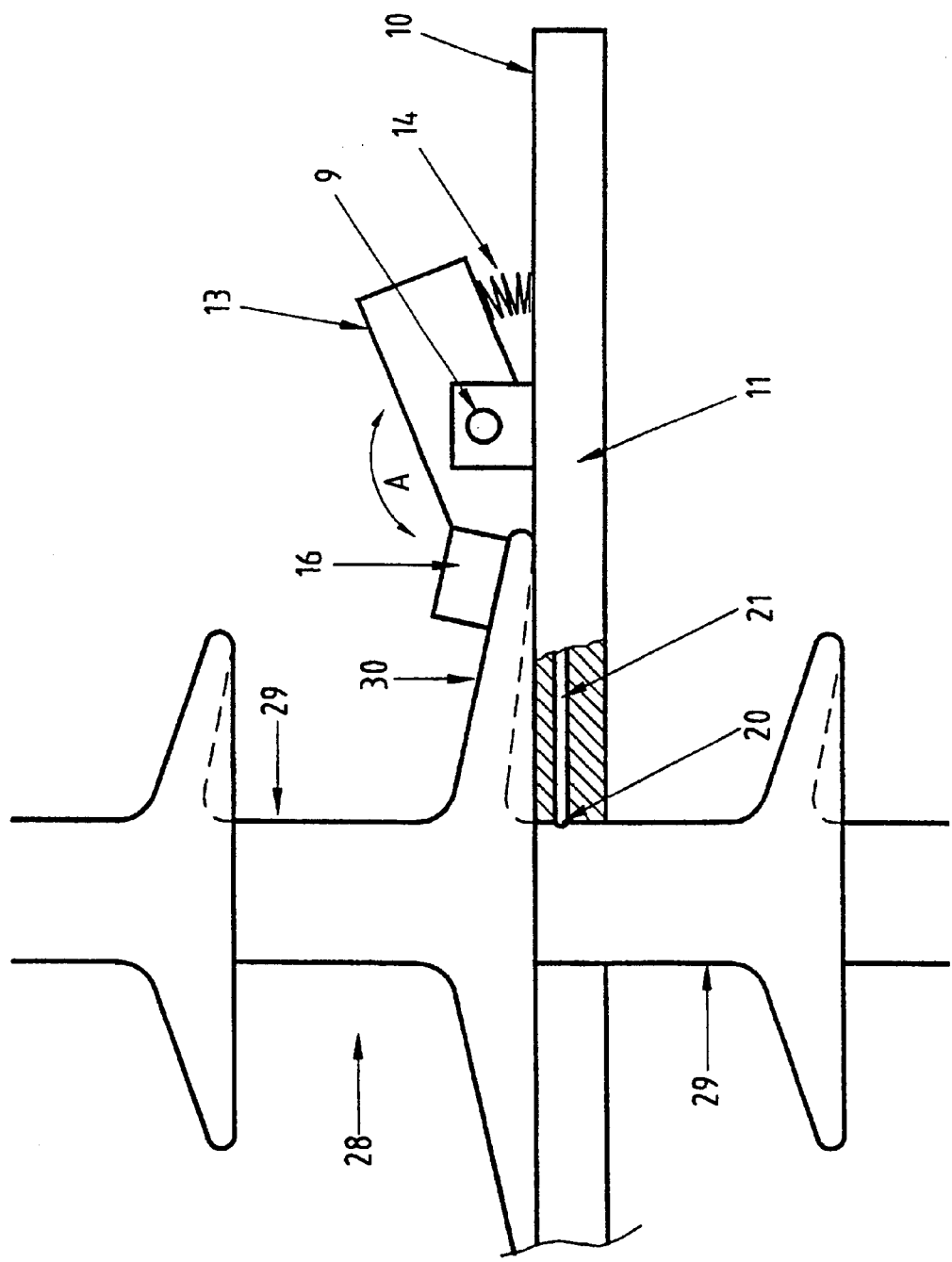
FIG. 4 is a schematic part-sectional elevational view showing the operation of the sampling head of FIG. 1.

When the platform 11 is urged against the rod 29, the release button 20 is depressed, causing the release of the locking pin 22 and turret 13. Through the action of the spring 14, the turret 13 snaps the cartridge 16 into position on the upper surface of the shed 30 as shown in FIG. 4. The spring 14 acting on the turret 13 ensures the correct pressure for sampling.

Figure 5:
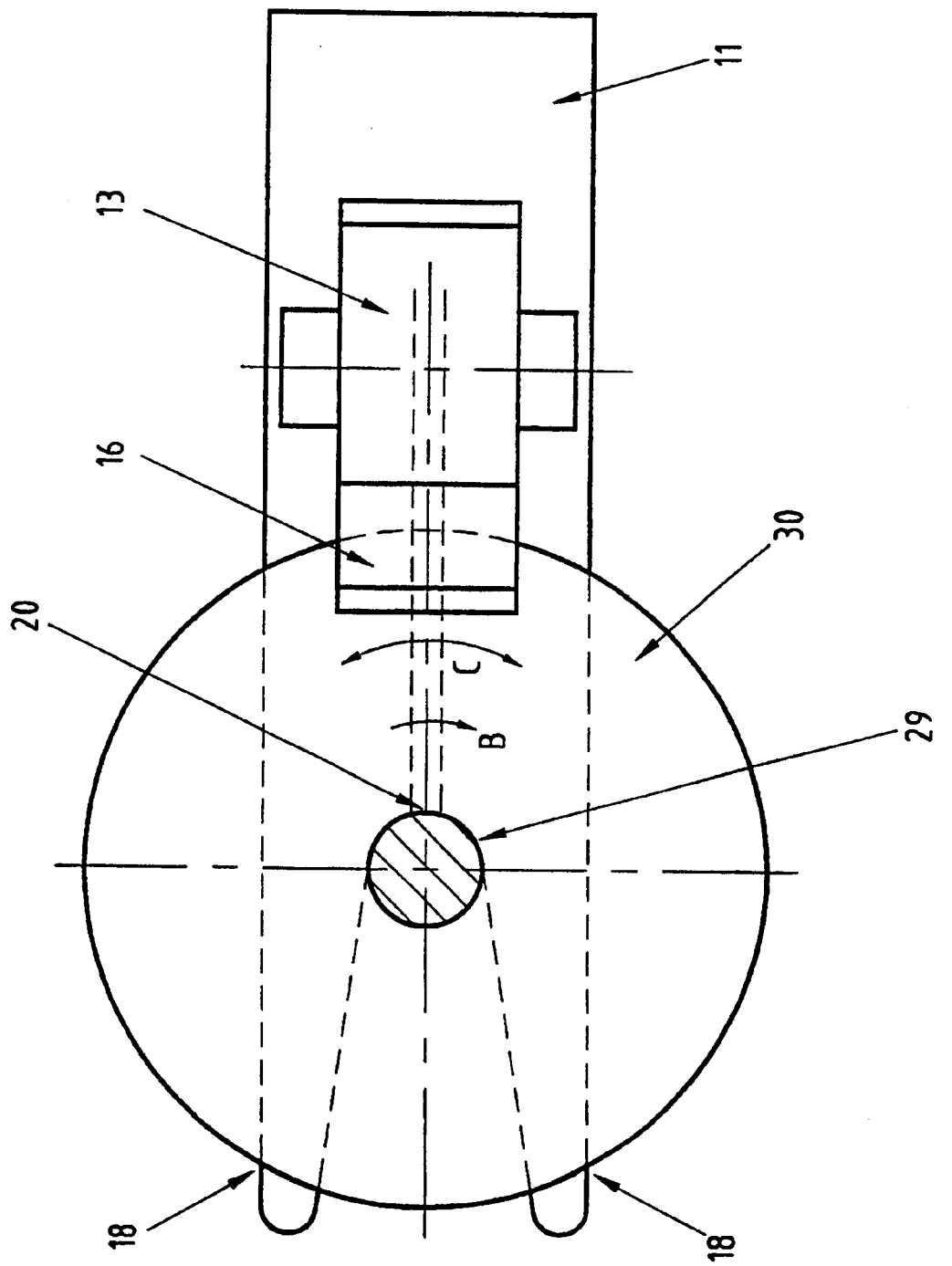
FIG. 5 is a schematic plan view showing the operation of the sampling head of FIG. 1.

If a sliver sample is to be obtained, the cartridge 16A is used. The sample is obtained by a smooth unidirectional movement of the platform around the rod depicted by arrow "B" in FIG. 5. If surface samples of an insulator are to be taken using either a cotton bud an abrasive pad, the cartridge 16B is used. In that case, several bidirectional movements (arrow "C") are normally executed to collect sufficient amount of polymeric material onto the abrasive pad or cotton swab from the surface of the insulator shed.

Once the samples have been obtained, the cartridges are preferably stored in sealed metallic containers to prevent contamination of the samples. The sliver or other sample is subsequently analysed to provide numeric indications of the condition of the line insulation.

The abovedescribed sampling apparatus and method enables a small sample of an insulator to be obtained during live line conditions in a safe and efficient manner.

The sampling tool can be manufactured easily and economically.

The spring 14 acting on the turret 13 ensures the correct pressure for sampling.

The foregoing describes only one embodiment of the invention, and modifications which are obvious to those skilled in the art may be made thereto without departing from the scope of the invention.

For example, the configuration of the sampling head may be changed to suit differently shaped insulators. The sampling head can be modified to sample the lower surface of the insulator sheds.

Further, the sampling cartridge may be mounted to the turret in any other suitable manner, or may form part of the turret. The release button may be replaced by any other mechanism to release the turret, such as a light sensor or proximity detector, or the turret may be released by the operator by remote control.

What is claimed is:

1. Apparatus for obtaining a sample of material of an insulator in a high voltage installation during live line conditions, the apparatus including
    a sampling head mounted to one end of a hot stick, and
    a sampling device mounted to the sampling head for collecting a sample of the insulator material at the surface of the insulator, upon manipulation of the hot stick by a user remote from the sampling device,
    wherein the sampling device has a planing blade adapted to cut a sliver from the surface of the insulator upon movement of the sampling device across the surface of the insulator.

2. Apparatus as claimed in claim 1, wherein the sampling device is a sampling cartridge removably mounted to the sampling head.

3. Apparatus as claimed in claim 1, wherein the sampling device has a receptacle adapted to collect the sliver cut from the surface of the insulator.

4. Apparatus for obtaining a sample of material of an insulator in a high voltage installation during live line conditions, the apparatus including
    a sampling head mounted to one end of a hot stick, and
    a sampling device mounted to the sampling head for collecting a sample of the insulator material at the surface of the insulator, upon manipulation of the hot stick by a user remote from the sampling device,
    wherein the sampling device includes a swab impregnated with a polymer solvent for collecting insulator material at the surface of the insulator.

5. Apparatus for obtaining a sample of material of an insulator in a high voltage installation during live line conditions, the apparatus including
    a sampling head mounted to one end of a hot stick, and
    a sampling device mounted to the sampling head for collecting a sample of the insulator material at the surface of the insulator, upon manipulation of the hot stick by a user remote from the sampling device,
    further comprising bias means on the sampling head for urging the sampling device against the surface of the insulator.

6. Apparatus as claimed in claim 5, further comprising a trigger mechanism operable by contact of the sampling head with the insulator, the bias means being actuated by the trigger mechanism.

7. Apparatus for obtaining a sample of material of an insulator in a high voltage installation during live line conditions, the apparatus including
    a sampling head mounted to one end of a hot stick, and
    a sampling device mounted to the sampling head for collecting a sample of the insulator material at the surface of the insulator, upon manipulation of the hot stick by a user remote from the sampling device,
    wherein the sampling head has a pair of spaced finger portions adapted to receive part of the insulator therebetween in use, to thereby position the sampling head relative to the insulator.

8. A sampling tool for obtaining a sample of material of an insulator in a high voltage installation during live line conditions, the sampling tool including a hot stick, a sampling head mounted to one end of the hot stick, a sampling device removably mounted to the sampling head, the sampling device having means thereon for collecting a sample of the insulator material at the surface of the insulator, bias means on the sampling head for urging the sampling device against the surface of the insulator, whereby in use, by manipulation of the hot stick by the user, the sampling device can be moved across the surface of the insulator while being urged thereagainst by the bias means to thereby collect said sample of the insulator material, and wherein said insulator is a solid polymeric material.

9. A method of taking a sample of material of an insulator in a high voltage installation during live line conditions using apparatus including a sampling head mounted to one end of a hot stick, and a sampling device mounted to the sampling head for collecting a sample of the insulator material at the surface of the insulator, upon manipulation of the hot stick by a user remote from the sampling device, the method including the step of manipulating the hot stick at a position remote from the sampling device to cause the sampling device mounted on the sampling head at the end of the hot stick to move across the surface of the insulator and collect a sample of the insulator material at the surface of the insulator, wherein the sampling device includes a planing blade, and the sample is obtained in the form of a sliver from the surface of the insulator.

10. A method of taking a sample of material of an insulator in a high voltage installation during live line conditions using apparatus including a sampling head mounted to one end of a hot stick, and a sampling device mounted to the sampling head for collecting a sample of the insulator material at the surface of the insulator, upon manipulation of the hot stick by a user remote from the sampling device, the method including the step of manipulating the hot stick at a position remote from the sampling device to cause the sampling device mounted on the sampling head at the end of the hot stick to move across the surface of the insulator and collect a sample of the insulator material at the surface of the insulator, wherein the sampling device includes a swab impregnated with a polymer solvent, and the sample is obtained as a swab sample of the surface of the insulator.

11. A method of taking a sample of material of an insulator in a high voltage installation during live line conditions using apparatus including a sampling head mounted to one end of a hot stick, and a sampling device mounted to the sampling head for collecting a sample of the insulator material at the surface of the insulator, upon manipulation of the hot stick by a user remote from the sampling device, the method including the step of manipulating the hot stick at a position remote from the sampling device to cause the sampling device mounted on the sampling head at the end of the hot stick to move across the surface of the insulator and collect a sample of the insulator material at the surface of the insulator, wherein the sampling head has bias means for urging the sampling device against the surface of the insulator, the method including the step of actuating the bias means to urge the sampling device against the surface prior to collecting a sample therefrom.

12. Apparatus for obtaining a sample of material of an insulator in a high voltage installation during live line conditions, the apparatus including a sampling head mounted to one end of a hot stick, and a sampling device mounted to the sampling head for collecting a sample of the insulator material at the surface of the insulator, upon manipulation of the hot stick by a user remote from the sampling device, wherein said insulator material is a solid polymeric material.

13. A method of taking a sample of material of an insulator in a high voltage installation during live line conditions using apparatus including a sampling head mounted to one end of a hot stick, and a sampling device mounted to the sampling head for collecting a sample of the insulator material at the surface of the insulator, upon manipulation of the hot stick by a user remote from the sampling device, the method including the step of manipulating the hot stick at a position remote from the sampling device to cause the sampling device mounted on the sampling head at the end of the hot stick to move across the surface of the insulator and collect a sample of the insulator material at the surface of the insulator, wherein said insulator material is a solid polymeric material.

* * * * *